United States Patent [19]

Takahashi et al.

[11] Patent Number: 4,537,973
[45] Date of Patent: Aug. 27, 1985

[54] PROCESS FOR PREPARING BIOTIN

[75] Inventors: Takeo Takahashi, Takarazuka; Kozo Shimago, Osaka; Kaoru Maeshima, Takarazuka, all of Japan

[73] Assignee: Sumitomo Chemical Company, Limited, Osaka, Japan

[21] Appl. No.: 309,765

[22] Filed: Oct. 8, 1981

Related U.S. Application Data

[63] Continuation of Ser. No. 129,732, Mar. 12, 1980, abandoned.

[51] Int. Cl.$^3$ .......................................... C07D 495/04
[52] U.S. Cl. .................................................. 548/303
[58] Field of Search ........................................ 548/303

[56]  References Cited

U.S. PATENT DOCUMENTS 3,740,416  6/1973  Gerecke et al. ..................... 548/303

OTHER PUBLICATIONS

McOmie, J., (Editor), *Protective Groups in Organic Chemistry*, Plenum Press, New York, 1973, pp. 196–198.
Kolasa, T., et al., *Tetrahedron*, 30, 3591–3595, (1974).
Yajima, H., et al., *Chem. Pharm. Bull. Japan*, 23(5), 1164–1166, (1975).
Yajima, H. et al., *J.C.S. Chem. Comm.*, 1974, pp. 107–108.
Bodanszky, M., et al., *Peptide Synthesis*, 2nd Ed., Wiley-Interscience, New York, 1976, pp. 44–45.

*Primary Examiner*—Richard A. Schwartz
*Attorney, Agent, or Firm*—Birch, Stewart, Kolasch & Birch

[57]  ABSTRACT

A process for preparing biotin, characterized in that a compound of the formula:

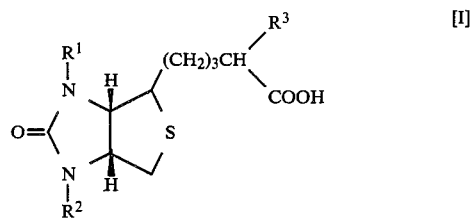

wherein $R^1$ and $R^2$ are each hydrogen or benzyl and $R^3$ is hydrogen or carboxyl, with the proviso that $R^1$ and $R^2$ are not simultaneously hydrogen, or a mixture of two or more different compounds of the formula [I] is heated in the presence of an alkanesulfonic acid.

13 Claims, No Drawings

PROCESS FOR PREPARING BIOTIN

This application is a continuation of application Ser. No. 129,732, filed on Mar. 12, 1980, now abandoned.

The present invention relates to a process for preparing biotin.

In this specification, the term "lower" is intended to mean a group having not more than eight carbon atoms, particularly having not more than five carbon atoms.

Biotin, the chemical name of which is cis-tetrahydro-2-oxothieno[3,4-d]-imidazoline-4-valeric acid, has an asymmetric carbon, and the term "biotin" in the present invention includes both of d-biotin and dl-biotin.

Biotin (also called "Vitamin H") is a valuable substance exerting a growth accelerative effect as well as a preventive and therapeutic effect on dermatoses, etc.

For the production of biotin, there is known a mehtod wherein 3,4-(1',3'-dibenzyl-2'-ketoimidazolido)-2-)ω-carboxybutyl)thiophane is heated under reflux in 48% hydrobromic acid to effect debenzylation (U.S. Pat. No. 3,740,416). However, this method is not favorable because it gives the objective compound only in a poor yield in spite of the troublesome operation due to the use of an irritative reagent.

As the result of an extensive study, an improved process for preparing biotin in an excellent yield with a high purity and without any disadvantage as seen in the said conventional process has been discovered.

Thus, the present invention provides an industrially advantageous process for preparing biotin which comprises heating a compound of the formula:

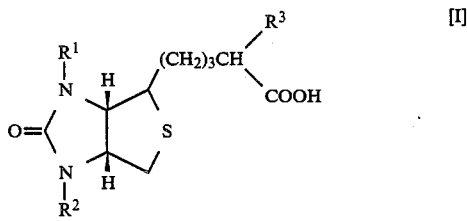

wherein $R^1$ and $R^2$ are each hydrogen or benzyl and $R^3$ is hydrogen or carboxyl, with the proviso that $R^1$ and $R^2$ are not simultaneously hydrogen in the presence of a lower alkanesulfonic acid.

According to the invention, a mixture of one part by weight of the starting compound [I] and 1 to 100 parts by weight, preferably 3 to 50 parts by weight, of a lower alkanesulfonic acid (e.g., methanesulfonic acid, ethanesulfonic acid, propanesulfonic acid) is heated at a temperature of 80° to 180° C., preferably of 110° to 150° C., for a period of 10 minutes to 20 hours, preferably of 0.5 to 10 hours. The reaction mixture is cooled and then admixed with water. Precipitated crystals are collected by filtration and recrystallized from water to give purified crystals of biotin.

It is not requisite but preferred to add to the reaction system a hydrocarbon having a boiling point higher than 100° C. (e.g., chlorobenzene, toluene, xylene, octane, decane, anisole) and/or an alkanoic acid, preferably having 2 to 4 carbon atoms (e.g., acetic acid, propionic acid), in order to minimize the formation of by-products and easily control the reaction temperature.

The starting compound [I] may be derived from 3,4-(1',3'-dibenzyl-2'-ketoimidazolido)-2-(ω,ω-di(lower)alkoxycarbonylbutyl)thiophane (hereinafter referred to as "compound [II]") by saponification; optionally followed by decarboxylation and/or partial debenzylation. Specific examples of the compound [II] are 3,4-(1',3'-dibenzyl-2'-ketoimidazolido)-2-(ω,ω-dimethoxycarbonylbutyl)thiophane, 3,4-(1',3'-dibenzyl-2'-ketoimidazolido)-2-(ω,ω-diethoxycarbonylbutyl)thiophane, 3,4-(1',3'-dibenzyl-2'-ketoimidazolido)-2-(ω-methoxycarbonyl-ω-ethoxycarbonylbutyl)thiophane, etc.

The starting compound [I] thus prepared may be separated from the reaction mixture and subjected to the process of the invention. However, it can be directly converted to biotin in situ, i.e., without separation from the reaction mixture. The typical example for preparing biotin from the compound [II] without separation of the compound [I] is illustrated below.

A mixture of the compound [II] and an aqueous lower alkanesulfonic acid (water content, usually not more than 40% by weight) is heated at a temperature of 40° to 100° C., preferably of 70° to 95° C., for 2 to 20 hours in the presence or absence of an alkanoic acid, preferably having 2 or 3 carbon atoms, whereby saponification proceeds to give a reaction mixture containing 3,4-(1',3'-dibenzyl-2'-ketoimidazolido)-2-(ω,ω-dicarboxybutyl)thiophane. The reaction mixture is continuously heated at a temperature of 100° to 180° C., preferably of 110° to 150° C., for 1 to 20 hours while distilling off volatile components (e.g., water, alcohols, esters), whereby decarboxylation and debenzylation proceed to give a reaction mixture containing biotin. The reaction mixture is worked up in the same manner as previously mentioned to give purified crystals of biotin.

This modified process for preparing biotin from the compound [II] without separation of the compound [I] constitutes one embodiment of the present invention.

The compound [II] is obtainable by reacting 3,4-(1',3'-dibenzyl-2'-ketoimidazolido)-1,2-trimethylenethiophanium bromide or d-camphor-sulfonate with a malonci diester according to U.S. Pat. Nos. 3,740,416 or 2,489,235.

As stated above, the process of this invention can advantageously afford biotin in an excellent yield with a high purity. It is particularly notable that biotin of high optical purity is obtainable by the use of the starting compound [I] which is optically active. Accordingly, this invention can provide an extremely important and valuable process for the synthesis of d-biotin which is, in particular, physiologically active.

Practical and presently preferred embodiments of the invention are illustratively shown in the following Examples.

EXAMPLE 1 d-Monobenzylbiotin (1.0 g) and methanesulfonic acid (3.0 g) are introduced into a 10 ml volume flask, and the flask is heated in an oil bath kept at 130° C. with vigorous stirring with a magnetic stirrer for 6 hours. The reaction mixture is cooled to room temperature and poured into 10 ml of ice water while stirring. Precipitated crystals are collected by filtration and recrystallized from water to give biotin (white needles, 0.58 g). Yield, 79%. M.P. 230° C. $[\alpha]_D^{20} = +91°$ (C=1 in 0.1% NaOH aq.).

REFERENCE EXAMPLE 1

Diethyl malonate (45.0 g) is dropwise added to a suspension of sodium methoxide (11 g) in toluene (200 ml) kept at 80° C., and the mixture is stirred for one hour while keeping this temperature. The reaction mixture is cooled to 50° C., 1-(−)-3,4-(1′,3′-dibenzyl-2′-ketoimidazolido)-1,2-trimethylenethiophanium bromide (30.0 g) is added thereto and the resultant mixture is heated under reflux for 4 hours. The reaction mixture is cooled to room temperature and admixed with water (270 g). The organic layer is separated, washed with water (250 g), dried and distilled in vacuo to give the residue primarily containing 1-(−)-3,4-(1′,3′-dibenzyl-2′-ketoimidazolido)-2-(ω,ω-diethoxycarbonylbutyl)thiophane. To the residue, there is added ethanol (160 g) containing 24.1% by weight of KOH, and the mixture is heated under reflux for one hour. By removing the solvent in vacuo, there is obtained the residue, which is admixed with water (300 g). The resulting mixture is neutralized with conc. hydrochloric acid and extracted with ethyl acetate. The organic layer is dried and distilled in vacuo to give the residue primarily containing 1-(−)-3,4-(1′,3′-dibenzyl-2′-ketoimidazolido-2-(ω,ω-dicarboxybutyl)thiophene.

EXAMPLE 2

Methanesulfonic acid (90.0 g) is added to the residue obtained in Reference Example 1, and the mixture is heated with stirring in an oil bath kept at 130° C. for 5 hours. The reaction mixture is cooled to room temperature, and ice cold water (270 g) is dropwise added thereto to give a slurry. The slurry is filtered with suction, and the obtained crystals are recrystallized from water to give d-biotin (white needles, 12.6 g). Yield, 77% (based on 1-(−)-3,4-(1′,3′-dibenzyl-2′-ketoimidazolido)-1,2-trimethylenethiophanium bromide). $[\alpha]_D^{20} = +91°$ (C=1 in 0.1% NaOH aq.).

EXAMPLE 3

Formic acid (75 g) and methanesulfonic acid (10.0 g) are added to the residue containing 1-(−)-3,4-(1′,3′-dibenzyl-2′-ketoimidazolido)-2-(ω,ω-diethoxycarbonylbutyl)thiophane, obtained in the same manner as in Reference Example 1, and the mixture is heated with stirring at 90° C. for 4 hours. By raising the temperature up to about 150° C., the low boiling point components are distilled off. The mixture is cooled to 100° C. again, admixed with additional methanesulfonic acid (150 g), and the mixture is heated with stirring at 140° C. for 4 hours. The reaction mixture is cooled and poured into ice water (500 g) to obtain a slurry. The slurry is treated in the same manner as in Example 2 to give d-biotin (12.3 g). Yield, 75.1% (based on 1-(−)-3,4-(1′,3′-dibenzyl-2′-ketoimidazolido)-1,2-trimethylenethiophanium bromide).

EXAMPLE 4

Methanesulfonic acid (200.0 g) and crude N,N-dibenzylbiotin (20.0 g) are introduced into a four-necked flask, and the mixture is stirred at 140° C. for 6 hours. The reaction mixture is cooled to a temperature between 10° and 15° C. and poured into ice water (1 l) while stirring. The precipitated crystals are collected by filtration and recrystallized from water to give d-biotin (white needles, 8.30 g). Yield, 72.0%.

EXAMPLE 5

Methanesulfonic acid (120 g) and acetic acid containing water (water content, about 40%) (50 ml) are added to the residue containing dl-3,4-(1′,3′-dibenzyl-2′-ketoimidazolido)-2-(ω,ω-diethoxycarbonylbutyl)thiophane, obtained in the same manner as in Reference Example 1 but using dl-3,4-(1′,3′-dibenzyl-2′-ketoimidazolido)-1,2-trimethylenethiophanium d-camphor-sulfonate (39.9 g) in place of 1-(−)-3,4-(1′,3′-dibenzyl-2′-ketoimidazolido)-1,2-trimethylenethiophanium bromide, and the resulting mixture is heated with stirring at a temperature of 93° to 95° C. for 6 hours. By raising the temperature to about 140° C., the low boiling point components are removed. Xylene (100 ml) is added to the residue, and the mixture is heated under reflux for 8 hours, during which a refluxing liquid predominantly containing xylene (about 30 ml) is removed from the reaction system. The reaction mixture is cooled to room temperature, the xylene layer is separated off and the remaining layer is poured into ice water (400 ml). The precipitated crystals are collected by filtration and recrystallized from water to give dl-biotin (white needles, 11.5 g). M.P. 233° to 235° C.

What is claimed is:

1. A process for preparing biotin, comprising: heating a mixture of a compound of the formula:

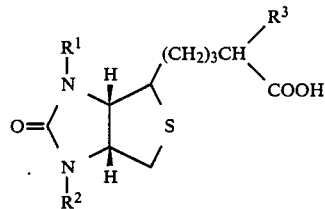

wherein $R^1$ and $R^2$ are each hydrogen or benzyl and $R^3$ is hydrogen or carboxyl, with the proviso that $R^1$ and $R^2$ are not simultaneously hydrogen and a lower alkanesulfonic acid at a temperature of 80° to 180° to form biotin and separating biotin from said mixture.

2. The process according to claim 1, wherein $R^1$ or $R^2$ is benzyl.

3. The process according to claim 1 or 2, wherein $R^3$ is hydrogen.

4. The process according to claim 1, wherein the lower alkanesulfonic acid is methanesulfonic acid.

5. The process according to claim 1, wherein the reaction is effected in the presence of a compound selected from the group consisting of a hydrocarbon having a boiling point higher than 100° C., an alkanoic acid having 2 to 4 carbon atoms and mixtures thereof.

6. The process according to claim 1, wherein the reaction is effected at a temperature of 110° to 150° C.

7. The process according to claim 1, wherein said lower alkanesulfonic acid is selected from the group consisting of methanesulfonic acid, ethanesulfonic acid and propanesulfonic acid.

8. The process according to claim 6, wherein said heating is performed for a period of 10 minutes to 20 hours.

9. The process according to claim 1, wherein said mixture contains one part by weight of the starting compound (I) and 1 to 100 parts by weight of said lower alkanesulfonic acid.

10. The process according to claim 6, wherein said heating is performed for a period of 0.5 to 10 hours.

11. The process according to claim 1, wherein said lower alkanesulfonic acid is an aqueous solution thereof.

12. The process according to claim 1, wherein said separating step includes admixing said reaction mixture with water thereby causing precipitation of biotin crystals and collecting said precipitated crystals.

13. A process for preparing biotin, comprising the steps of: heating a mixture of a compound of the formula:

3,4-(1',3'-dibenzyl-2'-ketoimidazolido)-2-(ω,ω-di(lower-)alkoxycarbonylbutyl)thiophane(II)
and an aqueous solution of a lower alkanesulfonic acid at a temperature of 40° to 100° C. to effect saponification of compound (II), and heating said mixture at a temperature of 100° to 180° C. to form biotin.

* * * * *